United States Patent [19]

Kitahara

[11] Patent Number: 4,658,790

[45] Date of Patent: Apr. 21, 1987

[54] AIR/FUEL RATIO DETECTING DEVICE AND CONTROL SYSTEM USING SAME

[75] Inventor: Tsuyoshi Kitahara, Ina, Japan

[73] Assignee: Nissan Motor Co., Ltd., Yokohama, Japan

[21] Appl. No.: 729,058

[22] Filed: Apr. 30, 1985

[30] Foreign Application Priority Data

May 1, 1984 [JP] Japan .................................. 59-88115
May 14, 1984 [JP] Japan .................................. 59-94685

[51] Int. Cl.⁴ .............................................. F02D 41/14
[52] U.S. Cl. .................................... 123/440; 123/489; 204/425
[58] Field of Search ................. 123/440, 489; 204/412, 204/406, 425, 15

[56] References Cited

U.S. PATENT DOCUMENTS

| | | | |
|---|---|---|---|
| 3,514,377 | 5/1970 | Spacil et al. | 204/1 |
| 4,499,880 | 2/1985 | Miki et al. | 123/489 |
| 4,568,443 | 2/1986 | Asayama et al. | 204/425 X |
| 4,578,171 | 3/1986 | Yamada et al. | 204/406 |
| 4,578,172 | 3/1986 | Yamada et al. | 123/489 X |
| 4,580,539 | 4/1986 | Kitahara | 123/440 |
| 4,591,421 | 5/1986 | Yamada et al. | 204/406 |
| 4,592,325 | 6/1986 | Nakagawa | 123/440 X |
| 4,594,139 | 6/1986 | Asayama et al. | 204/406 X |
| 4,601,809 | 7/1986 | Kitahara | 123/440 X |

FOREIGN PATENT DOCUMENTS 3239850  5/1984  Fed. Rep. of Germany .
143108  8/1983  Japan .................................. 123/489

Primary Examiner—Tony M. Argenbright
Attorney, Agent, or Firm—Schwartz, Jeffery, Schwaab, Mack, Blumenthal & Evans

[57] ABSTRACT

In order for increased precision control of air/fuel ratio, a pump electric current indicative voltage and a pump electric voltage are selectively used as an air/fuel ratio indicative signal in such a manner that the pump electric voltage is used at the stoichiometry, while the pump electric current indicative voltage is used as the air/fuel ratio indicative signal at an air/fuel ratio other than the stoichiometry. According to another aspect of the invention, the pump electric current indicative voltage is offset in response to step change in the pump electric voltage to generate an air/fuel ratio indicative signal which changes rapidly at the stoichiometry.

8 Claims, 12 Drawing Figures

AIR/FUEL RATIO DETECTING DEVICE AND CONTROL SYSTEM USING SAME

BACKGROUND OF THE INVENTION

The present invention relates to a device for detecting an air/fuel ratio of a fuel mixture by probing exhaust gas resulting from combustion of the fuel mixture, and more particularly to a device for detecting an air/fuel ratio of a fuel mixture combusted in an internal combustion engine. The present invention relates also to a system, employing an air/fuel ratio detecting device, for controlling an air/fuel ratio of a fuel mixture combusted in an engine.

Up until now, numerous types of exhaust gas sensors or oxygen sensors have been developed for the purpose of measuring the oxygen concentration within the exhaust gas resulting from combustion of a fuel mixture within an engine so as to detect the air/fuel ratio of the fuel mixture.

Laid-open Japanese patent application 56-89051 discloses an oxygen sensor. This oxygen sensor is illustrated in FIG. 1 for the ease of explanation. Referring to FIG. 1, this known oxygen sensor 1 operates on the principle of an oxygen concentration cell that produces an electromotive force in response to the ratio of the oxygen concentration on one side of a solid electrolyte to that on the opposite side thereof. It comprises a base 2 of alumina, a reference electrode 3 on the base 2, an oxygen ion-conductive solid electrolyte 4 which cooperates with the base 2 to enclose the reference electrode 3, a measurement electrode 5 interposing the solid electrolyte 4 in cooperation with the reference electrode 3. The above listed elements are covered by a protection layer of porous material. For activating the solid electrolyte, a heater 7 is embedded in the base 2. With the measurement electrode 5 exposed to the exhaust gas, an electric current Ip is supplied to the oxygen sensor 1 so as to cause migration of oxygen ion through the solid electrolyte 4, resulting in generation of a reference oxygen partial pressure Pa on the reference electrode 3 and an oxygen partial pressure Pb of the exhaust gas on the measurement electrode 5. Generation of the oxygen partial pressures Pa and Pb causes an electromotive force E to be generated which may be expressed by the following Nernst's equation as:

$$E=(RT/4F)\cdot \ln (Pa/Pb) \qquad (1)$$

where:
R = gas constant
T = absolute temperature
F = Faraday constant

With the same intensity of the electric current Is, the electromotive force E changes in a step manner at a predetermined air/fuel ratio. The air/fuel ratio where the E changes abruptly varies with variation in the intensity of the electric current Is.

An air/fuel ratio control system using the oxygen sensor 1 described above is known by the above mentioned laid-open Japanese patent application. According to this known air/fuel ratio control system, the intensity of the electric current Is is varied so that the rapid change in the electromotive force E takes place at a target air/fuel ratio. The electromotive force E is taken out as a sensor output voltage Vs. Since the characteristic of the sensor output voltage Vs is such that it remains constant irrespective of variation in air/fuel ratio after it has deviated by a small amount from a target air/fuel ratio, it is impossible to control the speed at which the actual air/fuel ratio is converged to the target one because the deviation cannot be determined by the sensor output voltage Vs having the above characteristic. Thus, there is the limitation to increasing the precision and response in detecting and controlling air/fuel ratio.

SUMMARY OF THE INVENTION

According to the present invention, a device for detecting an air/fuel ratio of a fuel mixture by probing exhaust gas resulting from combustion of the fuel mixture, comprises:

means for producing an oxygen ratio indicative signal indicative of the ratio of oxygen concentration within a sample gas receiving chamber adapted for receiving the exhaust gas to that within a reference gas receiving chamber adapted for receiving a reference gas;

means, including an oxygen ion-conductive solid electrolyte having thereon a pump cathode and a pump anode, for regulating the supply and discharge of oxygen to and from the sample gas receiving chamber in response to a pump electric current passing through the oxygen ion-conductive solid electrolyte between the pump cathode and anode;

means for controlling the intensity of the pump electric current so as to bring the oxygen ratio indicative signal into agreement with a reference;

means for detecting the intensity of the pump electric current and generating a pump electric current indicative signal;

means for detecting a pump electric voltage applied between said pump cathode and anode and generating a pump electric voltage indicative signal; and means receiving the pump electric current indicative signal and said pump electric voltage indicative signal for generating an air/fuel ratio indicative signal indicative of the air/fuel ratio.

According to a specific aspect of the present invention, the air/fuel ratio indicative signal generating means comprises means for allowing the pump electric voltage indicative signal to be generated as the air/fuel ratio indicative signal when the stoichiometry is to be detected and allowing the pump electric current indicative signal to be generated as the air/fuel ratio indicative signal when an air/fuel ratio other than the stoichiometry is to be detected.

According to another specific aspect of the present invention, the air/fuel ratio indicative signal generating means comprises means for comparing the pump electric voltage indicative signal with a reference and generating a comparison result indicative signal; means responsive to the comparison result indicative signal for generating an offset indicative signal; and means for combining the offset indicative signal with the pump electric current indicative signal and generating the result as the air/fuel ratio indicative signal.

An object of the present invention is to provide a device for detecting an air/fuel ratio which generates an air/fuel ratio indicative signal that continually varies versus the air/fuel ratio over a wide range from a rich range portion thereof to a lean range portion thereof and that varies rapidly at a predetermined air/fuel ratio, so that the precision, in detecting the air/fuel ratio over the wide range, is increased and the precision and response, in converging by feedback control the actual air/fuel ratio to the predetermined air/fuel ratio, is increased.

DESCRIPTION OF THE PREFERRED EMBODIMENTS

Figure 1:
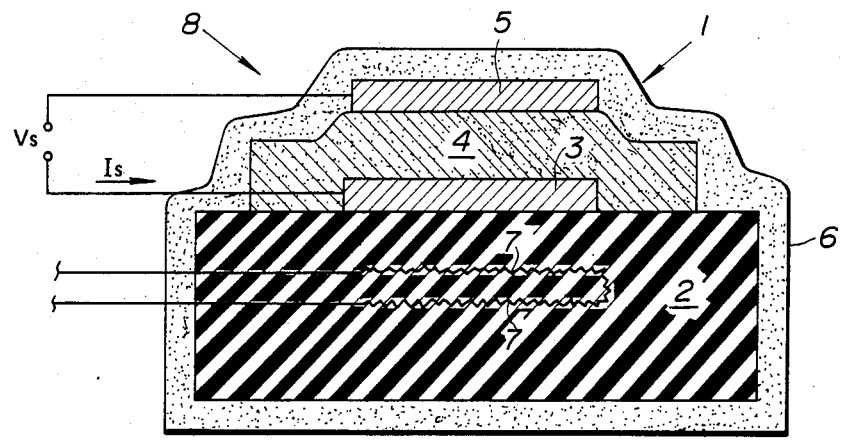
FIG. 1 is a sectional view of the known oxygen sensor discussed above.
Figure 2:
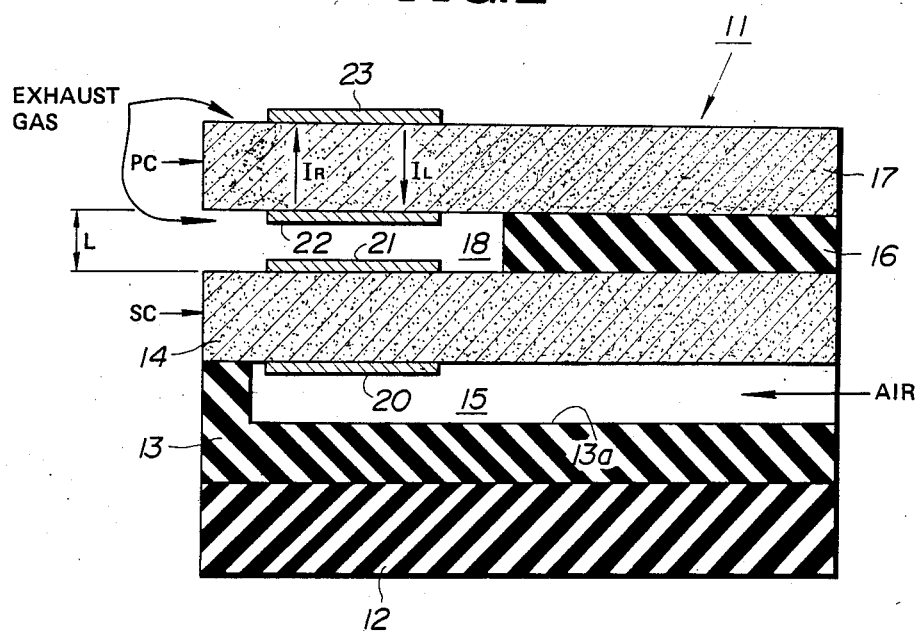
FIG. 2 is a longitudinal sectional view of an oxygen sensor used in the present invention.
Figure 3:
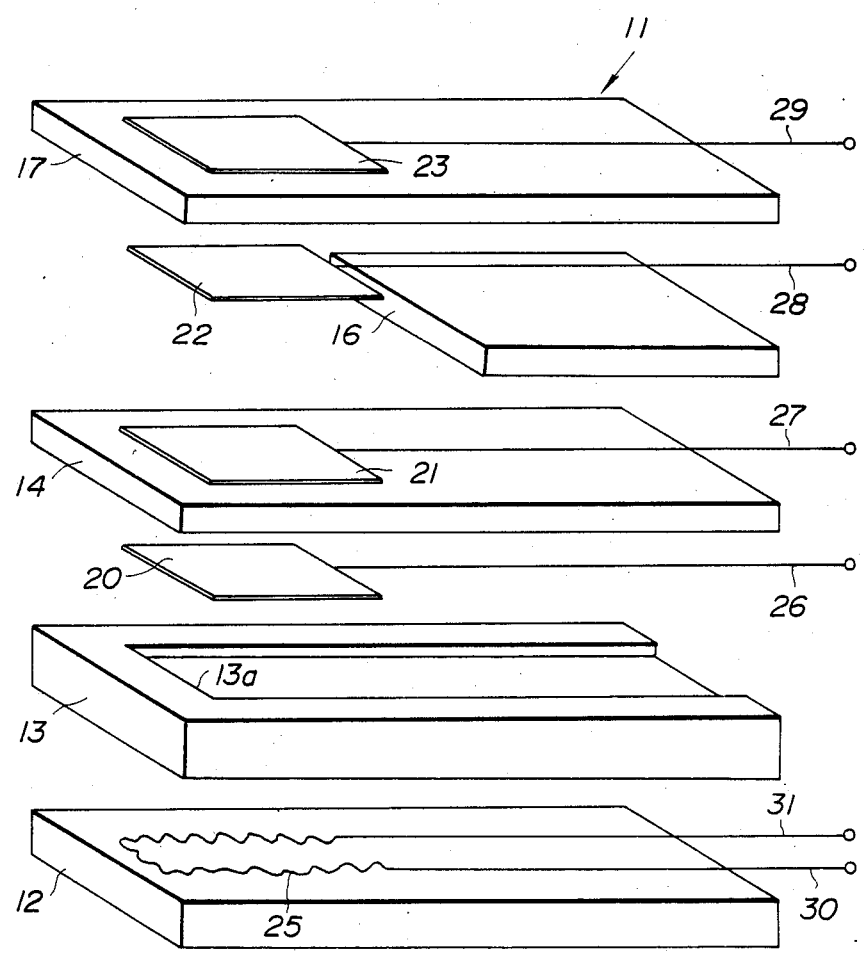
FIG. 3 is an exploded view of the oxygen sensor shown in FIG. 2.

Referring to FIGS. 2 to 7, a first embodiment according to the present invention is described. FIGS. 2 and 3 show a longitudinal sectional view of an oxygen sensor 11 and a perspective exploded view thereof, respectively. The oxygen sensor 11 comprises a base plate 12 of an insulating material such as alumina, a calibrated reference gas defining plate 13 formed with a gutter 13a laid on the base plate 12, and a first oxygen ion-conductive solid electrolyte plate 14 laid on the plate 13. The plate 13 and the first solid electrolyte plate 14 cooperate with each other to define within the gutter 13a a reference gas receiving chamber 15 for receiving a reference gas containing a predetermined oxygen concentration, such as an atmospheric air as is in this embodiment. Laid on the first solid electrolyte plate 14 is a spacer 16 with the thickness L. L is approximately 0.1 mm in this embodiment. Laid on this spacer 16 is a second oxygen ion-conductive solid electrolyte plate 17. This second solid electrolyte plate 17, spacer 16 and first solid electrolyte plate 15 cooperate with each other to define a sample gas receiving chamber 18 for receiving the exhaust gas resulting from combustion of a fuel mixture. The diffusion of gas from and to the chamber 18 is restricted by the very narrow span L between the first and second solid electrolyte plates 14 and 17.

Arranged on the opposite sides of the first solid electrolyte plate 14 are a sensor anode 20 (or a reference electrode) exposed to the atmospheric air within the reference gas receiving chamber 15 and a sensor cathode 21 (or a measurement electrode) exposed to the exhaust gas within the sample gas receiving chamber 18. The sensor cathode and anode 20, 21 and the first solid electrolyte plate 14 serves as a sensor cell SC which produces an electric voltage Vs indicative of the ratio of oxygen concentration within the sample gas receiving chamber 18 to that within the reference gas receiving chamber 15.

Arranged on the opposite sides of the second solid electrolyte plate 17 are a pump cathode 22 exposed to the exhaust gas within the sample gas receiving chamber 18 and a pump anode 23 exposed directly to the ambient exhaust gas atmosphere. The pump cathode and anode 22, 23 and the second solid electrolyte plate 17 serve as a pump cell PC which regulates the supply and discharge of oxygen to and from the sample gas receiving chamber 18 in response to a pump electric current Ip passing between the pump cathode and anode 22, 23 through the second solid electrolyte plate 17.

Printed on the adjacent side of the base plate 12 to the reference gas receiving plate 13 is a heater 25 (see FIG. 3) adapted to heat and activate the first and second solid electrolyte plates 14 and 17.

As shown in FIG. 3, the sensor anode 20 and sensor cathode 21 are connected with leads 26 and 27, respectively. The pump cathode 22 and pump anode 23 are connected with leads 28 and 29, respectively. The heater 25 is connected with leads 30 and 31.

The base plate 12, reference gas receiving plate 13 and spacer 16 are made of heat resistive insulating material, such as alumina, mullite. The solid electrolyte plates 14 and 17 are made of a sintered body obtained by solidifying $C_2O$, $MgO$, $Y_2O_2$, $YB_2O_3$ into an oxide such as $ZrO_2$, $HrO_2$, $ThO_2$, $Bi_2O_3$. The electrodes including sensor cathode and anode 20, 21 and pump cathode and anode 22, 23 include platinum or gold as a main constituent.

Although in this embodiment, the plates 14 and 17 are made of an oxygen ion-conductive solid electrolyte only, they may be partly formed of oxygen ion-conductive solid electrolyte such that that portion which is interposed between the associated electrodes 20 and 21 or 22 and 23 is formed of the oxygen ion-conductive solid electrolyte and the balance formed of another heat resistive material.

Figure 4:
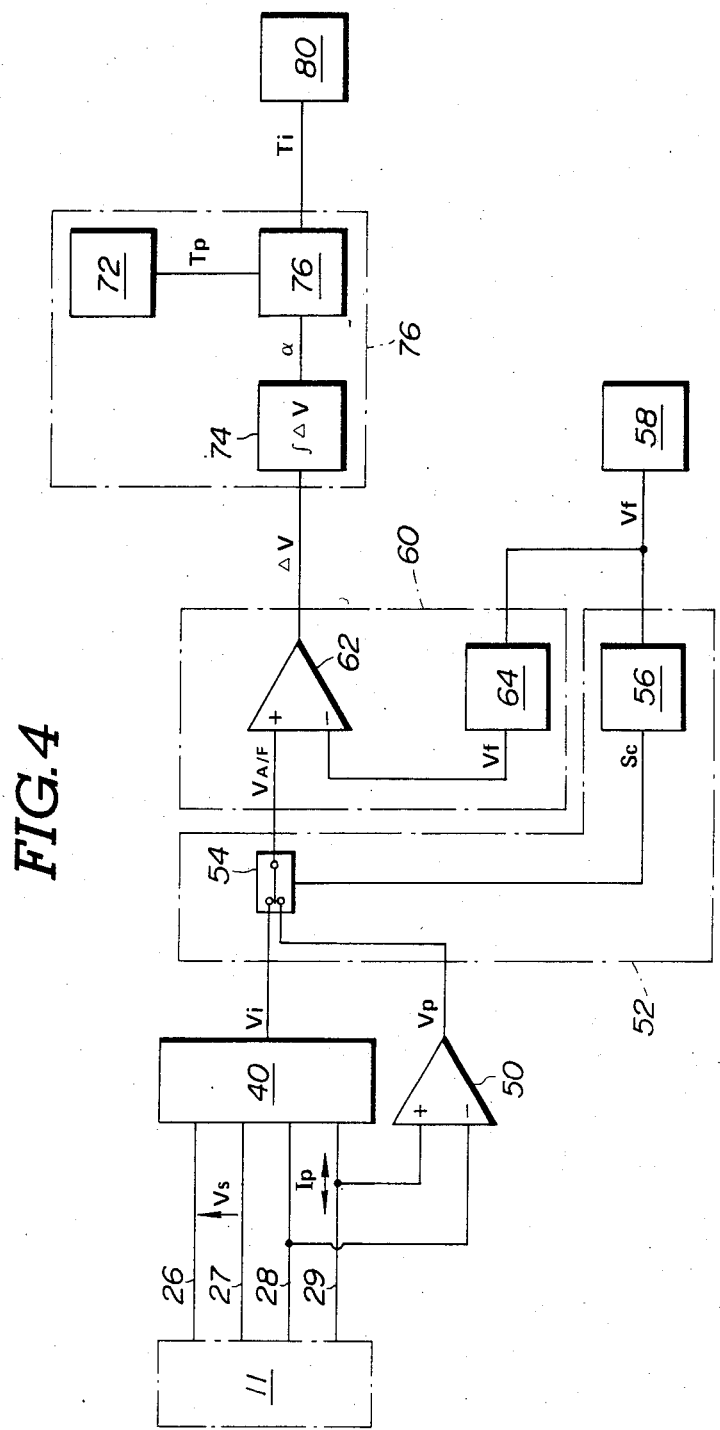
FIG. 4 is a schematic diagram showing a first embodiment according to the present invention.

As shown in FIG. 4, the oxygen sensor 11 has its sensor anode and cathode 20, 21 connected with a pump electric current supply and detection unit 40 via the leads 26, 27, resepectively, and its pump cathode and anode 22, 23 connected with the unit 40 via the leads 28, 29, respectively. The detailed structure of the unit 40 is shown in FIG. 5.

Figure 5:
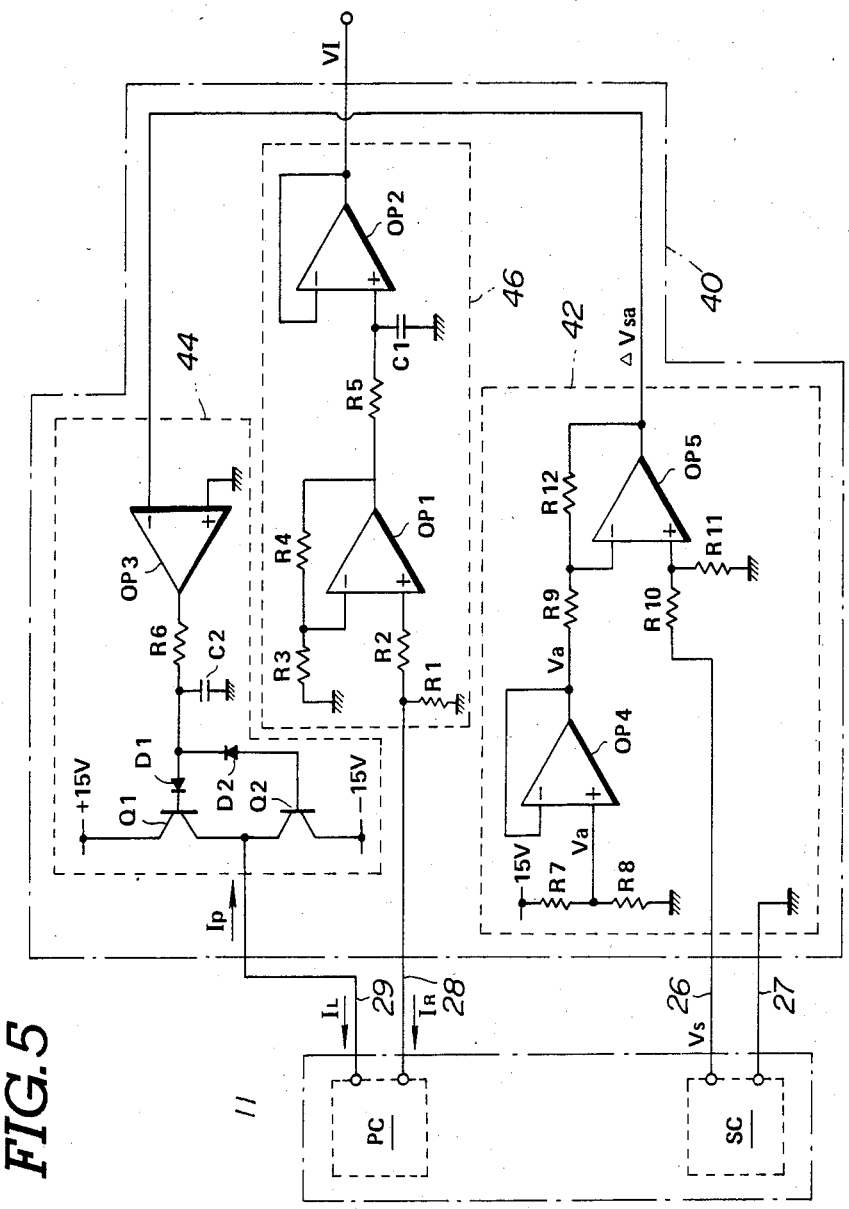
FIG. 5 is a circuit diagram of a pump electric current supply and detection unit.

Referring to FIG. 5, the electric voltage Vs produced by the sensor cell SC is compared with a reference voltage Va by a deviation detection circuit 42, which comprises two operational amplifiers OP4, OP5 and resistors R7, R8, R9, R10, R11, R12. The reference voltage Va should be set at a middle value between the upper and lower limits of step change of the output voltage Vs of the sensor cell SC which takes place with the oxygen concentration in the sample gas receiving chamber 18 kept at a predetermined value. In this embodiment, the reference voltage Va is obtained by dividing out the power source electric voltage 15 V by the resistors R7 and R8. The output voltage Vs and the reference voltage Va are fed to the operational amplifier OP5 where the reference voltage Va is subtracted from the output voltage Vs to cause generation of a deviation indicative signal $\Delta Vsa$ ($\Delta Vsa = K \cdot (Vs - Va)$, where: K=constant). The deviation indicative signal $\Delta Vsa$ is fed to a pump electric current supply circuit 44. Since the output voltage Vs indicates the oxygen concentration within the sample gas receiving chamber 18 and the reference voltage Va the above mentioned predetermined value, the deviation indicative signal $\Delta Vsa$ indicates a deviation of the oxygen concentration within the sample gas receiving chamber 18 from the predetermined value.

The pump electric current supply circuit 44 controls the intensity and direction of the pump electric current Ip supplied to the pump cell PC in response to the deviation $\Delta Vsa$ in such a manner as to reduce the deviation $\Delta Vsa$ toward zero so as to bring the output voltage Vs of the sensor cell SC into agreement with the reference voltage Va. The electric current supply circuit 44 comprises an operational amplifier OP3, a resistor R6, a condenser C2, and a complementary phase reverse circuit that is composed of transistors Q1, Q2 and diodes D1, D2.

The intensity and direction of the pump electric current Ip is detected by a pump electric current detection circuit 46 where a voltage drop across a resistor R1 is measured so as to generate a pump electric current indicative voltage Vi. The pump electric current detection circuit 46 comprises operational amplifiers OP7, OP2, a condenser C1 and resistors R2, R3, R4 in addition to the above mentioned resistor R1.

Referring back to FIG. 4, a pump electric voltage Vp, i.e., an electric voltage between the pump cathode and anode 22, 23, is detected by a pump electric voltage detection unit in the form of a differential amplifier 50. The output voltages Vi and Vp generated by the pump electric current detection unit 40 and the pump electric voltage detection unit 50 are fed to an air/fuel ratio indicative signal generation unit 52 which comprises an analog switch 54 and a selection signal generation circuit 56. The selection signal generation circuit 56 is supplied with a target air/fuel ratio indicative voltage Vf generated by a target air/fuel ratio setting unit 58 which retrieves and determines a target air/fuel ratio for the engine operating condition and generates a target air/fuel ratio indicative signal Vf. The selection signal generation circuit 56 generates a selection signal Sc that assumes a "H" (high) level or a "L" (low) level in response to the target air/fuel ratio indicative signal Vf. In this embodiment, the signal Sc assumes "L" level when the target air/fuel ratio indicative signal Vf indicates stoichiometry and "H" level when the target air/fuel ratio indicative signal Vf indicates the other air/fuel ratio. This signal Sc is fed to the analog switch 54, causing the switch 54 to allow the pump electric current indicative voltage signal Vi to be generated as an actual air/fuel ratio indicative signal $V_{A/F}$ when the selection signal Sc is at "H" level and to allow the pump electric voltage Vp to be generated as the actual air/fuel ratio indicative signal when the selection signal Sc is at "L" level. The actual air/fuel ratio indicative signal $V_{A/F}$ (Vi or Vp) is fed to a deviation computing unit 60 which comprises a differential amplifier 62 and a converter 64 that converts the target air/fuel ratio indicative signal Vf into a voltage having a level comparable with the above mentioned voltages Vi and Vp. Fed to the differential amplifier 62 are the actual air/fuel ratio indicative signal Vi or Vp and the target air/fuel ratio indicative signal Vf. Assuming now that the target air/fuel ratio is set at the stoichiometry, the pump voltage Vp is fed to the differential amplifier 62 where the target air/fuel ratio indicative signal Vf is subtracted from the pump voltage Vp to provide a deviation $\Delta V$ ($\Delta V = Vp - Vf$). Assuming that the target air/fuel ratio is set at an air/fuel ratio richer than or leaner than the stoichiometry, the pump electric current indicative voltage Vi is fed to the differential amplifier 62 where the target air/fuel ratio indicative signal Vf is subtracted from the pump electric current indicative voltage Vi to provide the deviation $\Delta V$ ($\Delta V = Vi - Vf$). The deviation indicative signal $\Delta V$ is fed to a fuel amount determination unit 70 which comprises a basic fuel injection amount computing section 72 generating a basic fuel injection amount indicative signal Tp, a feedback correction coefficient computing section 74 where the deviation $\Delta V$ is integrated to provide a feedback correction coefficient $\alpha$, and a final fuel injection amount computing section 76 where the basic fuel injection amount Tp is corrected with various correction coefficients including the feedback correction coefficient $\alpha$ to provide a final fuel injection amount Ti. The final fuel injection amount Ti is fed to a fuel supply device 80, such as a fuel injector installed at the engine intake manifold. The feedback correction coefficient $\alpha$ is provided for arithmetic operation on the deviation $\Delta V$ for integral control. If desired, the feedback correction coefficient may involve the term provided by arithmetic operation for differential control and the term provided by arithmetic operation for proportional control. As will be readily understood, the actual air/fuel ratio approaches toward the target air/fuel ratio at a correction rate that is dependent on the magnitude of the deviation $\Delta V$.

The above embodiment is further described in connection with the operation thereof.

In operation, the pump electric current supply circuit 44 supplies the pump electric current Ip to the pump cell PC so as to bring the voltage Vs into agreement with the reference voltage Va. Viz., when the oxygen concentration within the sample gas receiving chamber 18 drops below the above mentioned predetermined value, the pump electric current Ip is permitted to flow from the pump cathode 22 of the pump cell PC to the pump anode 23 thereof in a direction as indicated in FIG. 2 by an arrow $I_R$, causing migration of oxygen ion from the pump anode 23 to the pump cathode 22 so as to increase the oxygen concentration within the sample gas receiving chamber 18, while when the oxygen concentration with the sample gas receiving chamber 18 is higher than the predetermined value, the pump electric current Ip is permitted to flow from the pump anode 23 to the pump cathode 22 in a direction as indicated by an arrow $I_L$ in FIG. 2, causing migration of oxygen ions from the pump cathode 22 to the pump anode 23 so as to decrease the oxygen concentration within the sample gas receiving chamber 18.

In this embodiment, the reference voltage Va is set at 500 mV so as to maintain the oxgen concentration within the sample gas receiving chamber 18 at a predetermined value corresponding to the stoichiometry. Assuming that Pa=oxygen partial pressure within the reference gas receiving chamber 15, and Pb=oxygen partial pressure with the sample gas receiving chamber 18 and that the absolute temperature T of the exhaust gas is 1000° K., the oxygen partial pressure ratio Pb/Pa can be calculated by the Nernst's equation and $Pb/Pa = 10^{-10}$ holds. Since the oxygen partial pressure Pb is about 0.206 atm, then the oxygen partial pressure Pb can be expressed as:

$$Pb \approx 0.206 \times 10^{-10} \text{ atm.}$$

Assuming, now, that Pg=oxygen partial pressure within the ambient exhaust gas, the amount Q of oxygen molecule $O_2$ entering the sample gas receiving chamber 18 can be expressed as:

$$Q = D(Pg - Pb)$$

where: D=diffusion coefficient.
Since Pb is approximately zero (Pb≈0), $$Q \approx D \cdot Pg.$$

With the pump electric current Ip, the amount of $O_2$ as much as the amount Q is caused to move within the second solid electrolyte plate 17 so as to maintain the oxygen concentration within the sample gas receiving chamber 18 at the predetermined value. Since Ip is proportional to the amount Q which can be expressed as $Q \approx D \cdot Pg$, the intensity of the pump electric current Ip can be expressed as:

$$Ip \propto K1 \cdot Pg \qquad (2)$$

where: K1=constant.

Thus, the intensity of the pump electric current Ip is proportional to the oxygen partial pressure Pg within the exhaust gas.

When the air/fuel ratio to be detected is lean ($\lambda > 1$), the oxygen molecule $O_2$ is fed into the ambient exhaust gas from the sample gas receiving chamber 18 by pumping. Thus, the above equation (2) holds as it is.

On the other hand, when the air/fuel ratio to be detected is rich ($\lambda < 1$), the amount of oxygen molecule existing in the exhaust gas is very small and the oxygen partial pressure Pg falls in a range from about $10^{-20}$ to $10^{-25}$ (equilibrium oxygen partial pressure). Under this condition, much carbon dioxide $CO_2$ exists in the exhaust gas. Thus, in order to maintain the partial oxygen concentration within the sample gas receiving chamber 18 at the predetermined value of $0.206 \times 10^{-10}$, the pump electric current Ip is allowed to flow in a direction as indicated by an arrow $I_R$ in FIG. 2 so as to cause the oxygen molecule $O_2$ to move from the ambient exhaust gas to the sample gas receiving chamber 18, i.e., from the pump anode 23 to the pump cathode 22. On the surface of the pump anode 23 exposed to the ambient exhaust gas, the following reaction takes place:

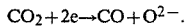

The oxygen ion $O^{2-}$ generated by the above reaction is caused to move through the second solid electrolyte 17 to enter the sample gas receiving chamber 18. Under this condition, there takes place on the surface of the pump cathode 22 a reaction as follows:

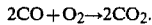

Thus, the oxygen $O_2$ having moved to the pump cathode 22 by pumping is consumed by this reaction. This means the intensity of the pump electric current Ip when the air/fuel ratio is rich indicates the amount of oxygen $O_2$ consumed by this reaction taking place on the pump cathode 22. The rate of the above reaction is proportional to the amount of CO diffused into the sample gas receiving chamber 18. With the above reaction, CO is also consumed until the CO partial pressure becomes zero, the amount Qco of CO can be expressed as:

$$Qco = D' \cdot (Pco - 0)$$
$$= D' \cdot Pco$$

where:
Pco=CO partial pressure in the exhaust gas,
D'=correction coefficient.

Therefore, the amount of $O_2$ pumped out from the ambient exhaust gas toward the sample gas receiving chamber 18 due to the pump electric current Ip is proportional to the concentration of CO within the ambient exhaust gas.

The concentration of CO (or CO+HC) is closely related to the air/fuel ratio when the air/fuel ratio is rich. Thus, the intensity of the pump electric current Ip is indicative of and variable with the air/fuel ratio.

Thus, the voltage Vi generated by the pump electric current detection circuit 46 (see FIG. 5) continually and gradually varies against the air/fuel ratio over a wide range from a rich range portion ($\lambda < 1$) to a lean range portion thereof ($\lambda > 1$).

Hereinafter, description is made regarding the pump electric voltage Vp between the pump anode 23 and pump cathode 22. The voltage Vp can be expressed as:

$$Vp = Ep + Ip \cdot Rp \qquad (3)$$

where:
Ep=electromotive force of PC
Rp=internal resistance of PC.

The electromotive force Ep can be expressed by the Nernst's equation as follows:

$$Ep = RT/4F \ln (Pg/Pb) \qquad (4).$$

As described before, when the reference voltage Va is set at 500 mV, the oxygen partial pressure Pb is maintained at around the predetermined value of $0.206 \times 10^{-10}$ atm. The oxygen partial pressure Pg within the ambient exhaust gas, on the other hand, is about $10^{-20}$ atm when the air/fuel ratio is rich ($\lambda < 1$) and it is about $10^{-2}$ atm when the air/fuel ratio is lean ($\lambda < 1$).

Figure 7:
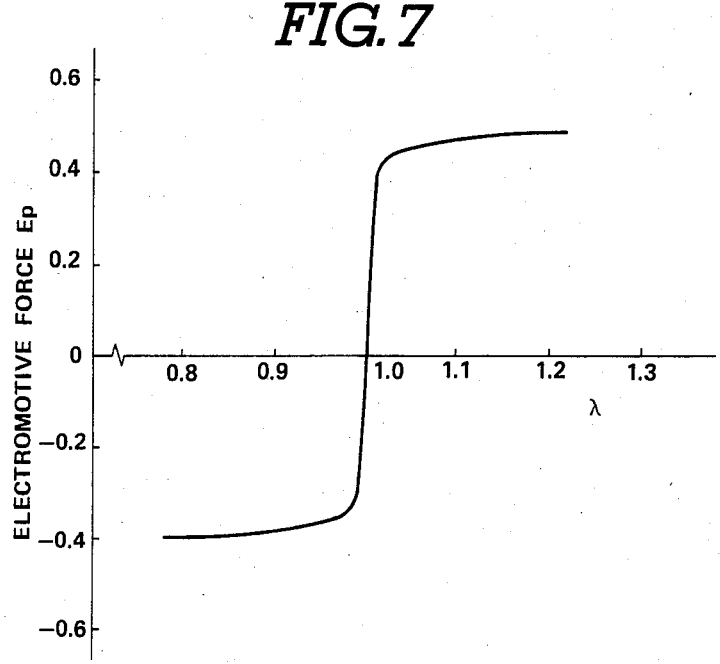
FIG. 7 shows pump electromotive force (Ep) versus A/F characteristic curve.

Assuming that T=1000° K., the electromotive force Ep which can be gievn by the equation (4) assumes about −400 mV to −500 mV when the air/fuel ratio is rich and it assumes about 400 mV to 500 mV when the air/fuel ratio is lean. Thus, the electromotive force Ep varies against air/fuel ratio (equivalent ratio: $\lambda$) as shown in FIG. 7.

Figure 6:
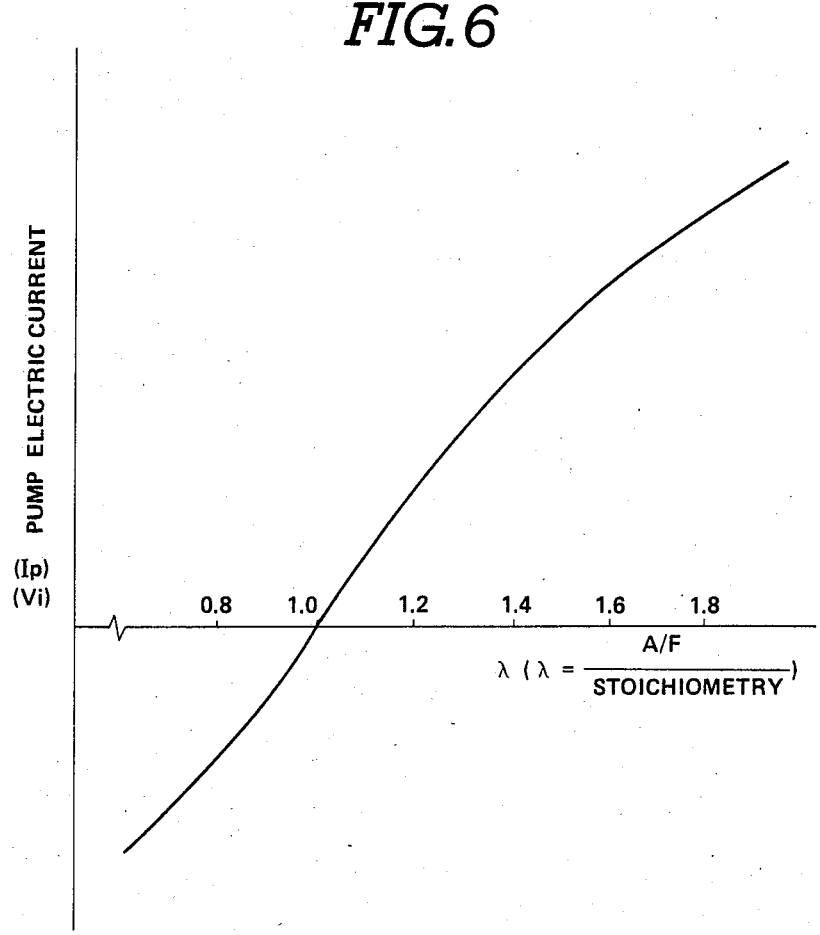
FIG. 6 shows pump current (Vi) versus A/F characteristic curve.

The internal resistance Rp is kept generally constant whether the air/fuel ratio is rich or lean as long as the temperature remains unchanged. The pump electric current Ip is proportional to the air/fuel ratio over a wide range the rich side to the lean side. Therefore, the term Ip·Rp of the equation (3) varies versus air/fuel ratio ($\lambda$) in the same pattern as the pump electric current Ip varies as shown in FIG. 6.

Figure 8:
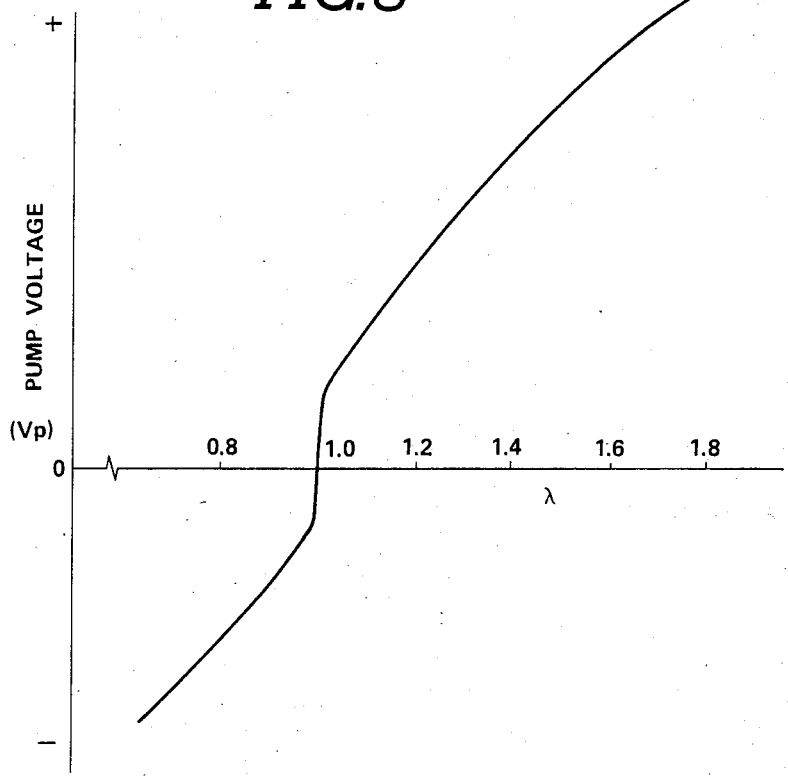
FIG. 8 shows pump voltage (Vp) versus A/F characteristic curve.

Therefore, the pump electric voltage Vp resulting from adding Ep to (Ip·Rp) as expressed by the equation (3) varies versus $\lambda$ as shown in FIG. 8. As will be readily appreciated from the characteristic curve of pump electric voltage Vp shown in FIG. 8, the electromotive force Ep governs the characteristic in the vicinity of the stoichiometry ($\lambda = 1$), while the pump electric current Ip governs the characteristic at the air/fuel ratio other than the stoichiometry. Step change in the pump electric voltage Vp near stoichiometry causes increased precision and response in detecting the stoichiometry ($\lambda=1$) because the electromotive force Ep is produced by the oxygen partial pressure near the pump anode 23 that is directly exposed to the ambient exhaust gas.

Because of the fact that the internal resistance Rp is variable depending upon the temperature, the pump electric voltage Vp could not be used to indicate the air/fuel ratio other than the stoichiometry unless the precise control of temperature is effected to keep it constant.

Referring to FIG. 4, the selection signal generation circuit 56 causes the analog switch 54 to feed the pump electric current indicative voltage Vi, as the air/fuel ratio indicative signal, to the differential amplifier 62 when the target air/fuel ratio is set at an air/fuel ratio other than the stoichiometry. With this voltage signal Vi, the precision is increased in detecting the air/fuel ratio over a wide range from rich range portion to lean range portion excluding the stoichiometry, thereby increasing the precision in bringing the air/fuel ratio into agreement with the target air/fuel ratio.

When the target air/fuel ratio is set at the stoichiometry, the selection signal generation circuit 56 causes the analog switch 54 to feed the pump electric voltage Vp, as the air/fuel ratio indicative signal, to the differential amplifier 62. With the step change characteristic of the pump electric voltage Vp near the stoichiometry, the precision and response in bringing the air/fuel ratio into agreement with the stoichiometry are increased.

It will now be appreciated that the present invention provides increased precision feedback control in bringing the air/fuel ratio into agreement with any target air/fuel ratio falling in a wide range excluding the stoichiometry, and increased precision feedback control, with high response, in bringing the air/fuel ratio into agreement with the stoichiometry whenever demanded to decrease exhaust emissions by increasing the rate of conversion within the three-way catalytic converter of the engine.

Although, in the first embodiment, the pump electric current indicative voltage Vi has been replaced with the pump electric voltage Vp when target air/fuel ratio is set at the stoichiometry, an air/fuel ratio indicative signal may be given by providing an offset to the pump electric current indicative voltage Vi in response to the result of comparison of the pump electric voltage Vp with a predetermined value. This is further described in connection with the second embodiment.

The second embodiment is described in connection with FIGS. 2, 3, 6, 7, 8, 9, 10 and 11.

Figure 9:
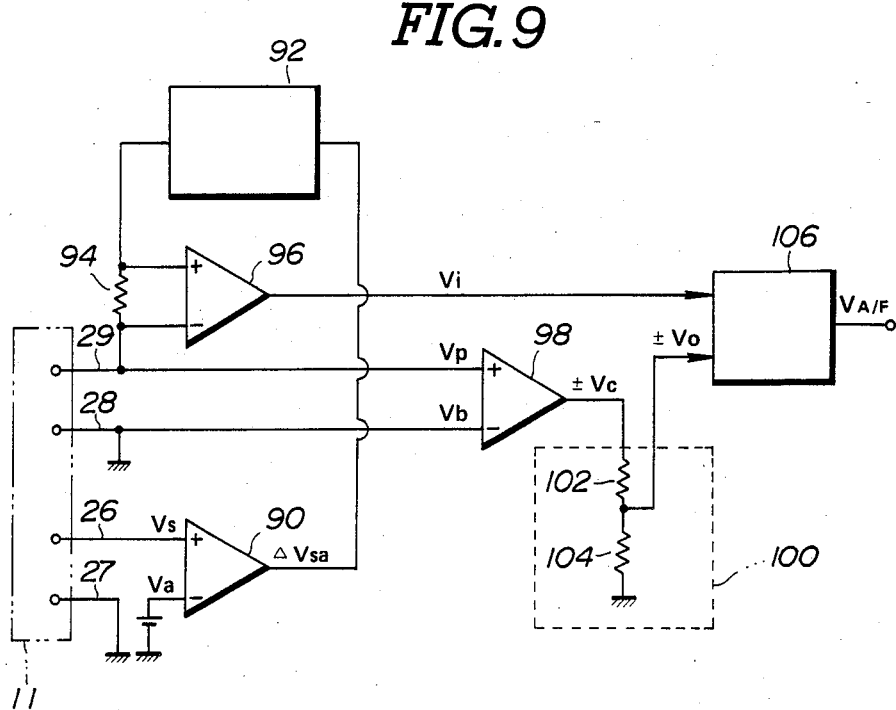
FIG. 9 is a schematic diagram showing a second embodiment according to the present invention.

Referring to FIG. 9, there is shown an air/fuel ratio detecting device using an oxygen sensor 11 shown in FIGS. 2 and 3.

Referring to the circuit shown in FIG. 9, an output voltage Vs of a sensor cell SC of an oxygen sensor 11 (ref. FIG. 3) and a reference voltage Va are fed to a differential amplifier 90 where Va is subtracted from Vs to cause generation of a deviation indicative signal $\Delta Vsa$ at its output.

The deviation indicative signal $\Delta Vsa$ is fed to a pump electric current supply circuit 92 which controls the intensity and direction of a pump electric current Ip supplied to a pump cell PC of the oxygen sensor 11 so as to reduce the deviation toward zero, thereby bringing the voltage Vs into agreement with the reference voltage Va (Vs=Va). The detailed structure is later described in connection with FIG. 10.

The pump electric current Ip supplied by the pump electric current supply circuit 92 to the pump anode 23 is detected in terms of a voltage across a resistor 94 by a differential amplifier 96 which generates this voltage as a pump electric current indicative voltage Vi.

In order to compare a pump electric voltage Vp with a predetermined reference voltage Vb (Vb=0 V in this embodiment), a comparator 98 is provided. The comparator 98 determines whether the pump voltage Vp is greater or less than the reference voltage Vb. In this embodiment, since Vb=0, the comparator 98 generates a predetermined positive voltage +Vc when Vp is greater than zero, while it generates a predetermined negative voltage −Vc when Vp is less than zero.

An offset indicative voltage signal generation circuit 100 is provided which is in the form of a series connected resistors 102, 104 forming a voltage divider. When +Vc is generated by the circuit 98, the circuit 100 divides this voltage +Vc and generates a first offset voltage +Vo. When −Vc is generated by the circuit 98, the circuit 100 divides this voltage −Vc and generates a second offset voltage −Vo.

An adder 106 is provided where the first or second offset voltage +Vo or −Vo is added to the voltage Vi generated by the differential amplifier 37 and the total is generated as an air/fuel ratio indicative signal $V_{A/F}$.

Figure 10:
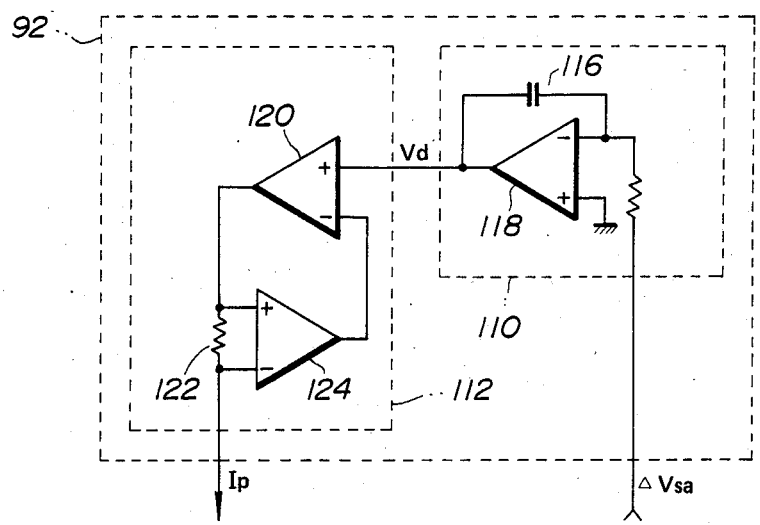
FIG. 10 is a circuit diagram of a pump current supply circuit.

Referring to FIG. 10, the structure of the pump electric current supply circuit 92 is described.

The pump electric current supply circuit 92 comprises a negative coefficient integral circuit 110 which integrates the deviation $\Delta Vsa$ to generate an integral Vd and a V−I converter circuit 112. The integral circuit 110 includes a resistor 114, a condensor 116, and an operational amplifier 118. In the integral circuit 110, the integral Vd is given by integrating the deviation $\Delta Vsa$ (Vd=$-K\int \Delta Vsa \cdot dt$, where: K=positive constant). The V−I converter circuit 112 comprises an operational amplifier 120, a resistor 122, and a differential amplifier 124. The differential amplifier 124 detects the corresponding voltage across the resistor 122 to the intensity of the pump electric current Ip and generates an output. Upon receipt of this output of the differential amplifier 124 and the integral Vd, the operational amplifier 120 controls the intensity and direction of the pump electric current Ip in response to the input signals.

This second embodiment may be readily understood from the following brief description.

The pump electric voltage Vp changes rapidly at the stoichiometry as shown in FIG. 8. Thus, the comparator 98 shown in FIG. 9 detects the stoichiometry ($\lambda=1$) where the pump voltage Vp changes rapidly after comparing the pump voltage Vp with the reference voltage Vb (Vb=0). Then, the offset indicative voltage generation circuit 100 generates the positive voltage +Vo to be added at the adder 106 to the pump electric current indicative voltage Vi when the pump voltage Vp is greater than zero, while it generates the negative voltage −Vo to be added at the adder 106 to the pump electric current indicative voltage Vi. Since this addition is effected in response to the step change of the pump electric voltage Vp, the air/fuel ratio indicative signal $V_{A/F}$ generated by the adder 106 provides increased precision and response in detecting the stoichiometry.

Figure 11:
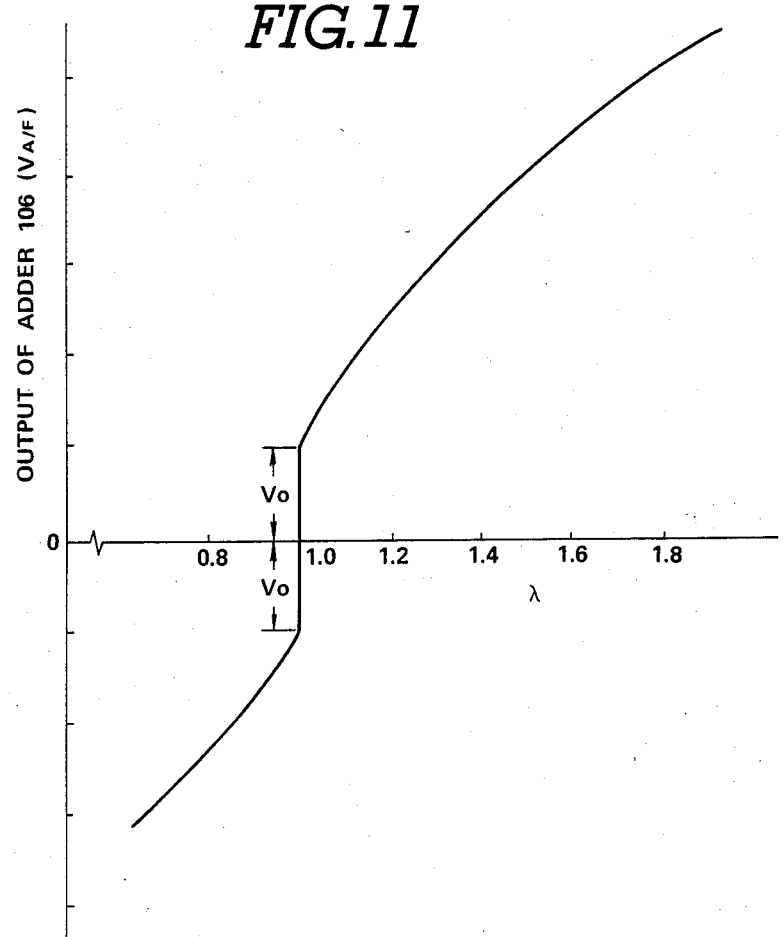
FIG. 11 shows $V_{A/F}$ versus A/F characteristic curve.

As shown in FIG. 11, the output $V_{A/F}$ of the adder 106 changes in a step manner (ON/OFF manner) at the stoichiometry ($\lambda=1$) and continually varies against the other air/fuel ratio.

Although, in the second embodiment, the reference voltage Vb is set at 0 V, the setting value is not limited to 0 V. In the case where the pump voltage Vp is used without any modification, any value between $-300$ mV and $+300$ mV may be used as a reference voltage Vb. In the case where the pump voltage Vp has been amplified or biased with a bias voltage, the reference value taking into the modification or bias voltage should be set as the reference voltage Vb.

Although, in the second embodiment, the first and second voltages $+Vo$ and $-Vo$ have the same magnitude, they may have different magnitudes or one of them may be set at 0 V. Although, in the second embodiment, the first and second voltages $+Vo$ and $-Vo$ have different polarities, two voltages with the same polarity may be used if the polarity of the input terminal of the adder is reversed in response to the input of one of the voltages to carry out subtraction of this voltage from the pump electric current indicative voltage Vi.

Figure 12:
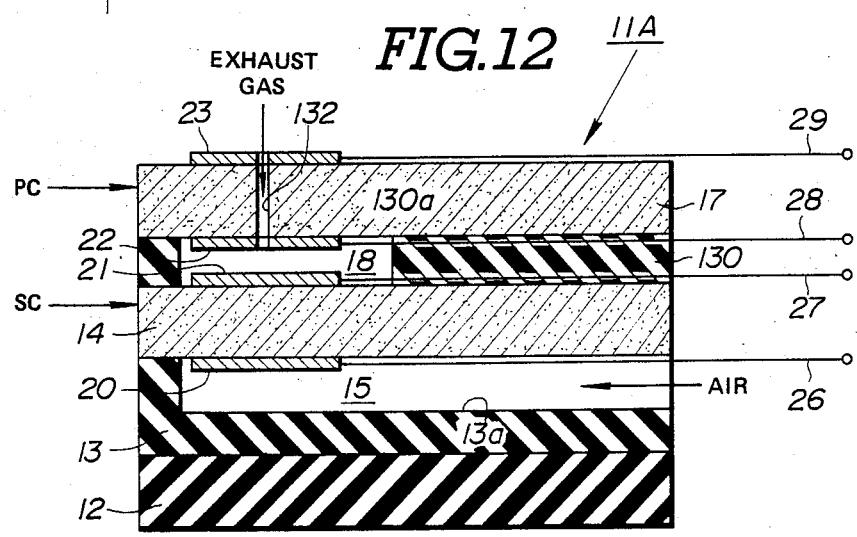
FIG. 12 is a longitudinal sectional view of a modified oxygen sensor.

Although, in the first and second embodiments, the oxygen sensor as illustrated in FIGS. 2 and 3 is used, a modified oxygen sensor as shown in FIG. 12 may be used.

Referring to FIG. 12, the modified oxygen sensor now designated by the reference numeral 11A is described. This oxygen sensor 11A is substantially the same as the oxygen sensor 11 except that there is interposed between a first solid electrolyte plate 14 and a second solid electrolyte plate 17 a spacer 130 formed with a window-like opening 130a, and a small hole 132 extending through a pump cathode 22, second solid electrolyte 17 and pump anode 23 serves as means for restricting gas diffusion. The first and second solid electrolyte plates 14, 17 and the spacer 130 cooperate to define within the window-like opening 130a a sample gas receiving chamber 18 communicating via the hole 132 with the ambient exhaust gas. The operation of this oxygen sensor is the same as that of the previously described oxygen sensor 11.

The other oxygen sensors as disclosed in a copending U.S. patent application Ser. No. 702,538—Tshuyoshi KITAHARA, filed on Apr. 2, 1985, may be used in the present invention. As means for restricting gas diffusion, a porous material may be used. Although in the described embodiments, the atmospheric air is used as the reference gas, another calibrated gas containing a predetermined oxygen concentration may be used as well.

What is claimed is:

1. A device for detecting an air/fuel ratio of a fuel mixture by probing exhaust gas resulting from combustion of the fuel mixture, comprising:
    means for defining a sample gas receiving chamber adapted for receiving the exhaust gas;
    means for restricting diffusion of gas from said sample gas receiving chamber and thereinto;
    means for defining a reference gas receiving chamber adapted for receiving a reference gas;
    means for producing an oxygen ratio indicative signal indicative of the ratio of oxygen concentration within said sample gas receiving chamber to that within said reference gas receiving chamber;
    means responsive to said oxygen ratio indicative signal for calculating a deviation of said oxygen ratio indicative signal from a reference and generating a deviation indicative signal;
    means, including an oxygen ion-conductive solid electrolyte having thereon a pump cathode and a pump anode, for regulating the supply and discharge of oxygen to and from said sample gas receiving chamber in response to a pump electric current passing through said oxygen ion-conductive solid electrolyte between said pump cathode and anode;
    means for controlling the intensity and direction of said pump electric current in response to said deviation indicative signal in such a manner as to reduce said deviation toward zero;
    means for detecting the intensity of said pump electric current and generating a pump electric current indicative signal;
    means for detecting a pump electric voltage applied between said pump cathode and pump anode and generating a pump electric voltage indicative signal; and
    means receiving said pump electric current indicative signal and said pump electric voltage indicative signal for generating an air/fuel ratio indicative signal indicative of the air/fuel ratio.

2. A device as claimed in claim 1, wherein said air/fuel ratio indicative signal generating means comprises:
    means for allowing said pump electric voltage indicative signal to be generated as said air/fuel ratio indicative signal when stoichiometry is to be detected and allowing said pump electric current indicative signal to be generated as said air/fuel ratio indicative signal when an air/fuel ratio other than stoichiometry is to be detected.

3. A device as claimed in claim 1, wherein said air/fuel ratio indicative signal generating means comprises:
    means for comparing said pump electric voltage indicative signal with a second reference and generating a comparison result indicative signal;
    means responsive to said comparison result indicative signal for generating an offset indicative signal; and
    means for combining said offset indicative signal with said pump electric current indicative signal and generating the result as said air/fuel ratio indicative signal.

4. A device as claimed in claim 3, wherein said combining means includes an adder.

5. A device as claimed in claim 1, further comprising:
    means for generating a target air/fuel ratio indicative signal; and
    wherein said air/fuel ratio indicative signal generating means comprises means for allowing said pump electric voltage indicative signal to be generated as said air/fuel ratio indicative signal when said target air/fuel ratio indicative signal indicates stoichiometry and allowing said pump electric current indicative signal to be generated as said air/fuel ratio indicative signal when said target air/fuel ratio indicative signal indicates an air/fuel ratio other than stoichiometry.

6. In a system for controlling air/fuel ratio of a fuel mixture supplied to an engine:
    means for retrieving a target air/fuel ratio for the engine operating condition and generating a target air/fuel ratio indicative signal;
    means for defining a sample gas receiving chamber receiving the exhaust gas resulting from combustion of the fuel mixture within the engine;
    means for restricting diffusion of gas from said sample gas receiving chamber and thereinto;

means for defining a reference gas receiving chamber receiving an ambient atmospheric air;

means for producing an oxygen ratio indicative signal indicative of the ratio of oxygen concentration within said sample gas receiving chamber to that within said reference gas receiving chamber;

means responsive to said oxygen ratio indicative signal for calculating a deviation of said oxygen ratio indicative signal from a reference and generating a deviation indicative signal;

means, including an oxygen ion-conductive solid electrolyte having thereon a pump cathode and a pump anode, for regulating the supply and discharge of oxygen to and from said sample gas receiving chamber in response to a pump electric current passing through said oxygen ion-conductive solid electrolyte between said pump cathode and anode;

means for controlling the intensity and direction of said pump electric current in response to said deviation indicative signal in such a manner as to reduce said deviation toward zero;

means for detecting the intensity of said pump electric current and generating a pump electric current indicative signal;

means for detecting a pump electric voltage applied between said pump cathode and pump anode and generating a pump electric voltage indicative signal; and means receiving said pump electric current indicative signal and said pump electric voltage indicative signal for generating an air/fuel ratio indicative signal indicative of the air/fuel ratio.

7. The combination as claimed in claim 6, wherein said air/fuel ratio indicative signal generating means comprises:

means for allowing said pump electric voltage indicative signal to be generated as said air/fuel ratio indicative signal when said target air/fuel ratio indicative signal indicates stoichiometry and allowing said pump electric current indicative signal to be generated as said air/fuel ratio indicative signal when said target air/fuel ratio indicative signal indicates an air/fuel ratio other than stoichiometry.

8. The combination as claimed in claim 6, wherein said air/fuel ratio indicative signal generating means comprises:

means for comparing said pump electric voltage indicative signal with a second reference and generating a comparison result indicative signal;

means responsive to said comparison result indicative signal for generating an offset indicative signal; and means for combining said offset indicative signal with said pump electric current indicative signal and generating the result as said air/fuel ratio indicative signal.

* * * * *